United States Patent
Rajasekharan et al.

(10) Patent No.: US 12,163,937 B2
(45) Date of Patent: Dec. 10, 2024

(54) DETECTION OF PER AND POLYFLUOROALKYL SUBSTANCES USING TOTAL ORGANIC FLUORIDE

(71) Applicant: Hach Company, Loveland, CO (US)

(72) Inventors: Vishnu Vardhanan Rajasekharan, Fort Collins, CO (US); Cary Burton Jackson, Fort Collins, CO (US); Matthew Ryan Salzer, Loveland, CO (US); Dan Jonathan Kroll, Fort Collins, CO (US)

(73) Assignee: HACH COMPANY, Loveland, CO (US)

( * ) Notice: Subject to any disclaimer, the term of this patent is extended or adjusted under 35 U.S.C. 154(b) by 186 days.

(21) Appl. No.: 17/580,215

(22) Filed: Jan. 20, 2022

(65) Prior Publication Data
US 2023/0228726 A1   Jul. 20, 2023

(51) Int. Cl.
*G01N 1/40*    (2006.01)
*G01N 31/00*   (2006.01)
*G01N 33/18*   (2006.01)

(52) U.S. Cl.
CPC ....... *G01N 31/005* (2013.01); *G01N 33/1826* (2013.01); *G01N 1/405* (2013.01); *Y10T 436/193333* (2015.01); *Y10T 436/196666* (2015.01); *Y10T 436/25125* (2015.01)

(58) Field of Classification Search
CPC . Y10T 436/196666; Y10T 436/193333; Y10T 436/25125; G01N 31/005; G01N 33/1826; G01N 1/4044
USPC ................................................. 436/125, 126
See application file for complete search history.

(56) References Cited

U.S. PATENT DOCUMENTS

| | | | |
|---|---|---|---|
| 5,073,502 A | * | 12/1991 | Steele ............... G01N 33/0049 122/93 |
| 2019/0185352 A1 | * | 6/2019 | Chiang ................. C02F 1/283 |
| 2024/0102960 A1 | * | 3/2024 | Rajasekharan .... G01N 27/4163 |

FOREIGN PATENT DOCUMENTS

WO    WO2020236435 A1    11/2020

OTHER PUBLICATIONS

Wagner, A. et al. "Determination of adsorbable organic fluorine from aqueous environmental samples by adsorption to polystyrene-divinylbenzene based activated carbon and combustion ion chromatography," J. Chromatogr. A 1295 (2013) 82-89 (Year: 2013).*
Schaefer, C.E. et al. "Electrochemical treatment of poly- and perfluoroalkyl substances in brines," Environ. Sci.: Water Res. Technol., 2020, 6, 2704-2712 (Year: 2020).*

* cited by examiner

*Primary Examiner* — Jennifer Wecker
*Assistant Examiner* — Michelle Adams
(74) *Attorney, Agent, or Firm* — Oliff PLC

(57) ABSTRACT

An embodiment provides a method for deriving an amount of PFAS substances from a total organic fluoride measurement in a sample, including: removing inorganic fluoride from the sample using one or more of an ion exchange cartridge and an exclusion apparatus; preconcentrating, using a solid phase extraction, at least one PFAS substance in the sample; digesting, using a working electrode and a counter electrode, the at least one PFAS substance to an amount of total organic fluoride; and determining, using an analyzer, the amount of total organic fluoride in the sample. Other aspects are described and claimed.

18 Claims, 11 Drawing Sheets

DETECTION OF PER AND POLYFLUOROALKYL SUBSTANCES USING TOTAL ORGANIC FLUORIDE

FIELD

This application relates generally to measurement and detection of polyfluoroalkyl or perfluoroalkyl substances in a sample, and, more particularly, to measurement and detection of polyfluoroalkyl or perfluoroalkyl substances using total organic fluoride in a sample.

BACKGROUND

Ensuring water quality is critical in a number of industries such as, drinking water, pharmaceuticals, and other manufacturing fields. Additionally, ensuring water quality is critical to the health and well-being of humans, animals, and plants which are reliant on the water for survival. Per and polyfluoroalkyl substances (PFAS), and per fluoro octanoic acid substances (PFOA), are a large class of synthetic chemicals that impacts public health at ultra-low levels. Governments and regulating agencies have set limits on PFAS concentration. Such limits may be set upon the PFAS compounds in surface water, ground water, wastewater, biosolids, and soils. Several industries that use or have used PFOS/PFOA are replacing with alkyl fluoro substitutes which still are of concern.

BRIEF SUMMARY

In summary, one embodiment provides a method for deriving an amount of PFAS substances from a total organic fluoride measurement in a sample, comprising: removing inorganic fluoride from the sample using one or more of an ion exchange cartridge and an exclusion apparatus; preconcentrating, using a solid phase extraction, at least one PFAS substance in the sample; digesting, using a working electrode and a counter electrode, the at least one PFAS substance to an amount of total organic fluoride; and determining, using an analyzer, the amount of total organic fluoride in the sample.

Another embodiment provides a method for deriving an amount of perfluoroalkyl substances from a total organic fluoride measurement in a sample, comprising: removing inorganic fluoride from the sample using one or more of an ion exchange cartridge and an exclusion apparatus; preconcentrating, using a solid phase extraction, at least one perfluoroalkyl substance (PFAS) in the sample; digesting, using a working electrode and a counter electrode, the at least one perfluoroalkyl substance to an amount of total organic fluoride; and determining, using an analyzer, the amount of total organic fluoride in the sample.

A further embodiment provides a device for deriving an amount of PFAS substances from a total organic fluoride measurement in a sample, comprising: a digestion chamber; an exclusion apparatus; an ion exchange cartridge; an analyzer; and the device for deriving a PFAS substances from a total organic fluoride measurement in a sample being configured to: remove inorganic fluoride from the sample using one or more of the ion exchange cartridge and the exclusion apparatus; preconcentrate, using a solid phase extraction, at least one PFAS substance (PFAS) in the sample; digest, in a digestion chamber, using a working electrode and a counter electrode, the at least one PFAS substance to an amount of total organic fluoride; and determine, using an analyzer, the amount of total organic fluoride in the sample.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
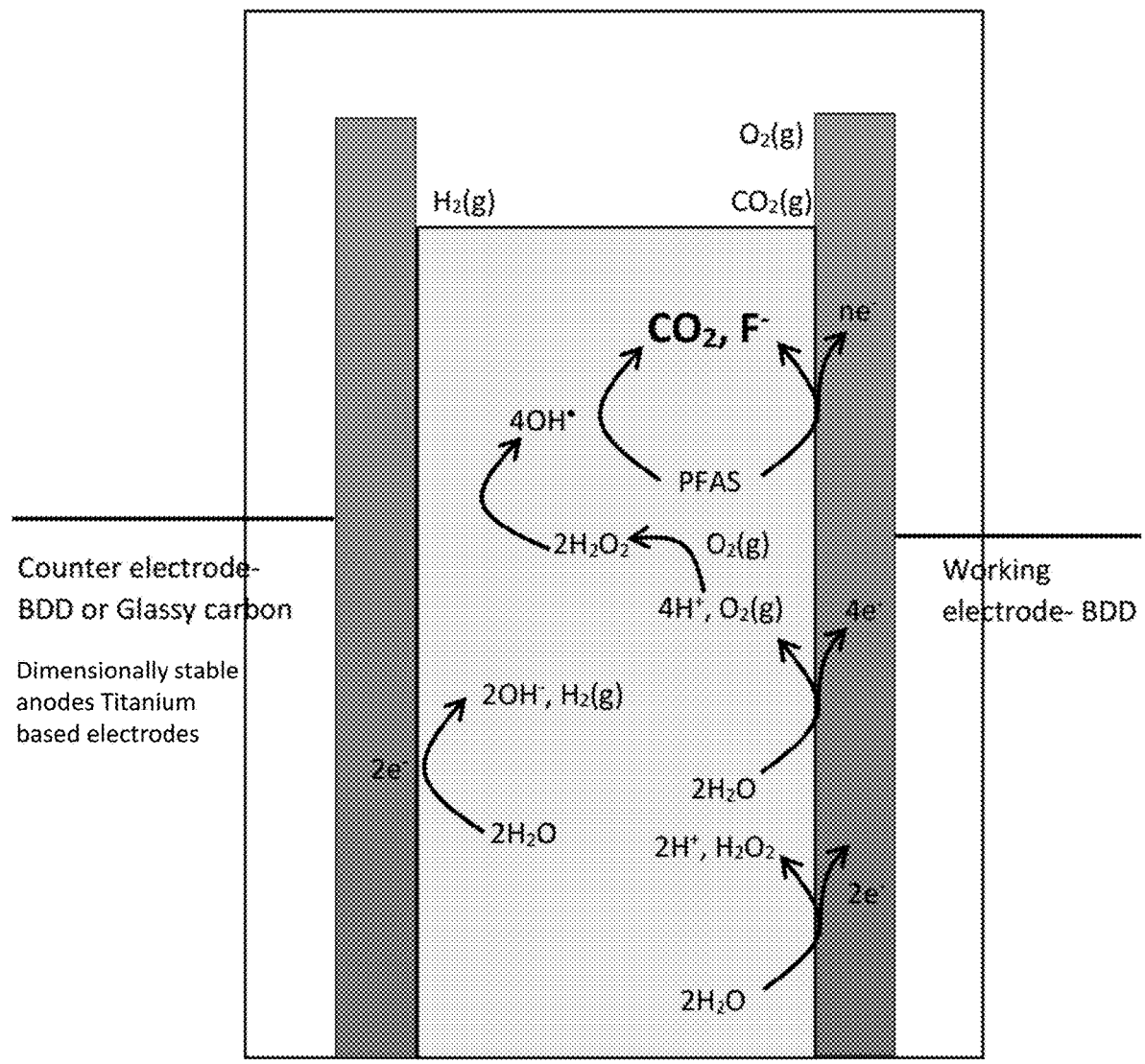
FIG. 1 illustrates example reactions in a digestion cell for measurement of PFAS substances in a sample.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Per and polyfluoroalkyl substances (PFAS) are large class of synthetic chemicals that impacts public health at ultra-low levels, even in the range of part-per-trillion (ppt). The current Environmental Protection Agency in the United States health advisory states 70 ng/L maximum for PFOS and PFOA in drinking water and recommends total organic fluoride (TOF) at 1 µg/L as a surrogate measurement of fluorine compounds in surface water, ground water, wastewater, biosolids and soils. Other governments have mandated regulatory limits for PFAS compounds. Significant investment is made by treatment plants to achieve these limits. Many of these treatment methodologies are not entirely validated. Several industries that used PFOS/PFOA are replacing with alkyl fluoro substitutes, and these replacements remain a health and environmental concern. Very few high-end lab methods are approved by agencies for PFAS analysis. No technologies exist for analyzing PFAS in field settings. In many cases field analysis of these parameters is impractical due to the complex sample preparation needed in the existing methods.

There are many challenges to TOF measurement which may be critical for detection of per and polyfluoroalkyl substances. For example, a method and system require an ultra-low-level detection of a diverse set of compounds. The PFOS/PFOA compounds have a widespread presence in the environment. The difficulty of degradation of larger molecules to recalcitrant smaller ones, precursor transformations, changes in the chemical structure after discharge from an industry or during the leaching process from a landfill, and high background during the analysis of TOF since most tap water has 0.5 to 1 ppm inorganic fluoride anion background from city treatment. Additionally, there are a wide variety of locations and conditions to be tested such as military bases, airports, industrial plants, landfills, firefighting training sites, or the like. Some tests only measure a limited set if targeted chemical and precursors, and fail to identify all PFAS compounds.

Specifically, some methods to detect PFAS compounds have limitations. For example, combustion ion chromatography may have inefficient adsorption of organic and inorganic fluoride activated carbon. The method may have the added step to elute inorganic fluoride eluted from the activated carbon by washing with neutral nitrate solution. There remains a complex process of burning the TOF loaded activated carbon burnt in an oxygen stream under pyro hydrolytic conditions. This may produce toxic gaseous byproducts of the combusted activated carbon trapped in an absorption medium where corrosive hydrogen fluoride is formed during combustion process. The corrosive hydrogen fluoride is then condensed back into the solution that dissociates to form fluoride anion. A separate aliquot of known volume of the absorbing solution that contains fluoride anion is then injected into an ion chromatograph that is complex in nature by means of a sample injection valve. This requires long cycle times for the halide anions to be separated on the anion separation column of the ion chromatograph (IC). Additionally, conductivity of the eluent needs to be reduced with an anion suppression device prior to the IC conductivity detector where fluoride is measured.

What is needed is an accurate and simpler method for TOF measurement for PFAS analysis. For example, it is advantageous to eliminate the combustion cartridge, to avoid the production of hydrogen fluoride gas in the conventional TOF, and production of oxidants without reagents during the digestion process. Efficiency of hydroxyl radical generation is higher on boron-doped diamond (BDD) electrodes since there is a weak interaction between the radicals and BDD. The robustness of BDD may provide a long term stability under harsh conditions, high current densities, fluctuating pH, and complex solution matrices. A bipolar electrode configuration may be used to increase oxidation efficiencies PFAS. Treatment efficacy validation can be achieved through this total organic fluoride, and total oxidizable precursor measurements. This may be achieved by digesting the PFAS on BDD electrodes and detecting fluoride optically.

Accordingly, the systems and methods described herein provide a technique for measurement of PFAS and PFOS substances in a sample. In an embodiment, the method may use total organic fluoride as a substitute to derive all the PFAS concentration in a sample. In an embodiment, a combustion cartridge and resulting hydrogen fluoride gases may be eliminated. Oxidants may be produced without reagents during a digestion process. In an embodiment, a BDD electrode may be produce hydroxyl radicals. In an embodiment, a sample may be collected in a PFAS free container. A pretreatment may be performed to quantify total inorganic fluoride. The pretreatment may also concentrate PFAS in the sample. In an embodiment, a digestion may use electrochemical (Echem) oxidization in a digestion cell. The digestion cell may have a working electrode and/or a counter electrode. One or more of the electrodes may be a BDD electrode. In an embodiment, the digestion cell may have a recirculating feature. The recirculation may use sample volume movement, heating, mixing, reagent detection, in-situ fluoride detection (for digestion validation), bubble mitigation, or the like. In an embodiment, an analyzer may measure total organic fluoride. The analyzer may use fluorometric, colorimetric techniques, an optical measurement device, an electrochemical cell, a chromatographic device, or the like.

The illustrated example embodiments will be best understood by reference to the figures. The following description is intended only by way of example, and simply illustrates certain example embodiments.

In an embodiment, the described method and system may simplify the total organic fluoride analysis. For example, elimination of the combustion cartridge, and hence avoiding the production of hydrogen fluoride gas in the existing total organic fluoride (TOF). Also, the system and method may produce oxidants without reagents during the digestion process. Additionally, efficiency of hydroxyl radical generation may be higher on the BDD electrodes since there is a weak interaction between the radicals and BDD. The robustness of BDD provides long term stability under harsh conditions, high current densities, fluctuating pH, and complex solution matrices. There are also options to use bipolar electrode configuration to increase oxidation efficiencies PFAS Treatment efficacy validation can be achieved through this total organic fluoride, and total oxidizable precursor measurements. This is achieved by digesting the PFAS on BDD electrodes and detecting fluoride optically. FIG. 1 shows the primary steps through which the Echem process takes place.

Referring to FIG. 1, in an embodiment, a diagram of steps in the electrochemical (Echem) cell are illustrated. At the working electrode, PFAS may be directly oxidized to carbon dioxide and fluoride. This is likely to occur for lower chain PFAs compounds. PFAS may be indirectly oxidized by hydroxyl radicals. Hydroxyl radicals may be generated by two ways. Water oxidation may produce hydrogen peroxide or oxygen. Hydrogen peroxide may dissociate to form hydroxyl radicals. Oxygen may form superoxide which then reacts with protons to form hydrogen peroxide. This hydrogen peroxide can then disassociate and produce hydroxyl radicals. In an embodiment, at a counter electrode water may be reduced to form hydroxide anions and hydrogen gas.

Figure 2:
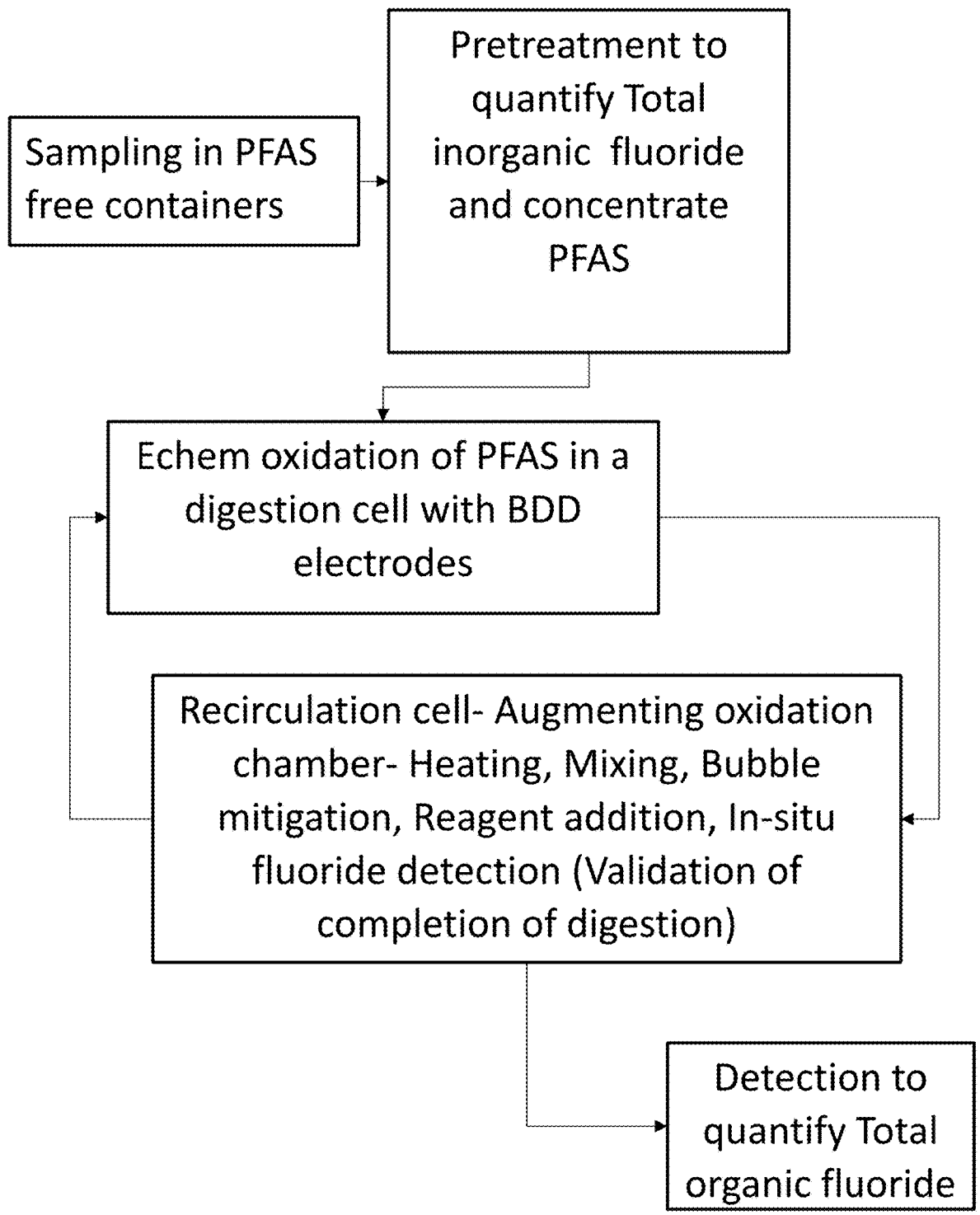
FIG. 2 illustrates an example workflow of a method for measuring PFAS in a sample.

Referring to FIG. 2, in an embodiment, a simplified workflow of a method is illustrated. In an embodiment, after sampling the PFAS it then may be pretreated to remove the fluoride and preconcentrate the PFAS. The pre-concentrated PFAS then may be digested in a recirculated Echem cell. This may enable the complete oxidation of PFAS to Fluoride. Relative changes in the fluoride concentration in the Echem cell due to PFAS oxidation may be monitored in the recirculation cell.

In an embodiment, the system and method may have four steps. A first step, comprises removal of inorganic fluoride using ion exchange cartridges. A second step, comprises a pre-concentration and/or speciation using solid phase extraction by cartridges. A third step, comprises digestion using voltage and/or current application on BDD to break down PFAS to fluoride. A fourth step, comprises detection of fluoride using fluorometric and/or colorimetric techniques. The steps are numbered numerically for ease of reading. The steps may be rearranged or selected independently.

Figure 3:
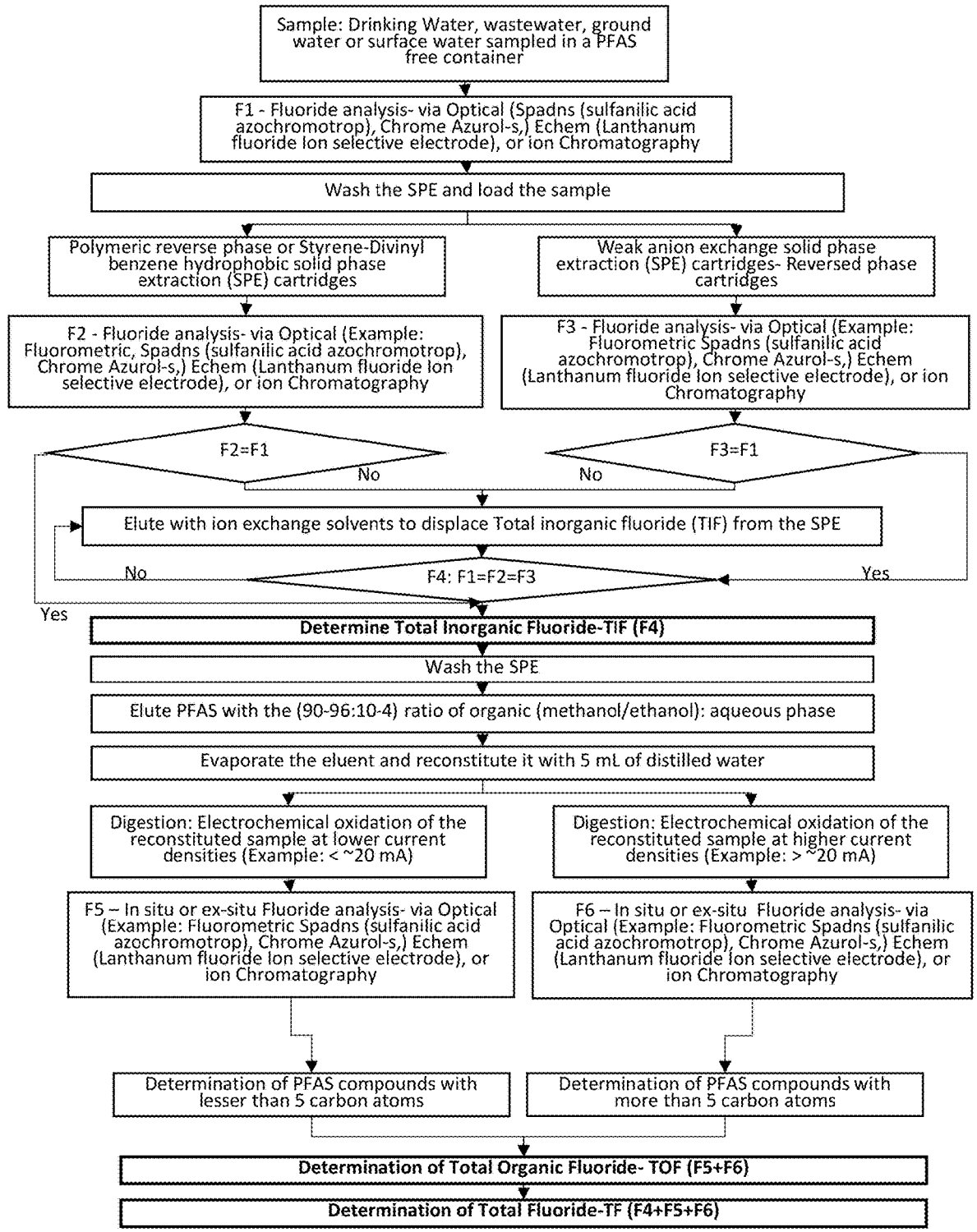
FIG. 3 illustrates flow diagram of an analysis of a sample with PFAS substances.

Referring to FIG. 3, in an embodiment, an example analysis of a sample is illustrated. In an embodiment, a sample may collected. The sample collection may be in a PFAS free material adhering to protocols that are required to obtain a true representation of the field sample. In an embodiment, inorganic fluoride present in the sample may be analyzed using optical, Echem or chromatographic methods.

In an embodiment, the sample may be divided into two portions. One portion is loaded into hydrophobic solid phase extraction (SPE) cartridges (Ex. polymeric reverse phase or styrene-divinyl benzene). A second portion may be loaded into weak anion exchange cartridge. This step may be used to speciate between lower (<C5) and higher (>C5) carbon chain PFAS compounds from a sample. For example, the lower carbon chain PFAS compounds will not be retained by the polymeric hydrophobic cartridges. Even though the weak anion exchange cartridges may retain the lower carbon chain PFAS compounds, it has the propensity to retain the inorganic fluoride. Solid phase extraction may be used for preconcentrating the PFAS to achieve the necessary regulatory limits (Ex. up to 70 ng/L detection limits). Custom cartridges will be used for pre-concentration and speciating. Cartridges may be selected based upon a particular use, type of sample, regulatory limits, or the like.

The fluoride content may be determined in both the wash solutions to determine the amount of fluoride retained in addition to the retention of the PFAS compounds (F2 and F3). If the fluoride content (F1) in the sample is different from F2 or F3 then ion exchange eluent like nitrate or hydroxides may be used to completely elute F—while PFAS is retained in the solid phase. Once F1=F2=F3 the total inorganic fluoride (TIF) is determined and labelled as F4.

After the determination of TIF, the SPE cartridges are washed. A mixture of an organic species (for example, methanol) and water with ammonium acetate at 90:10 or 96:4 ratio is used to elute the PFAS compounds. This eluent, if needed, is then evaporated and reconstituted with 5 mL water.

Both the fractions may be digested. For lower carbon chain PFAs compounds a lower current density is applied. For higher current density would be required to digest the higher carbon chain compounds. Longer chain PFOA/PFOS and harder to oxidize species like PFBS, PFHxS and Gen-X may be oxidized on BDD with additional catalyst (for example, HOOH, manganese, ozone).

Fluoride is detected from both the fractions (F5 and F6). Lower level detection of fluoride will be enabled by fluorometric metric methods. The sum of F5 and F6 may be the total organic fluoride and the sum of F4+F5+F6 would be the Total fluoride.

Figure 4:
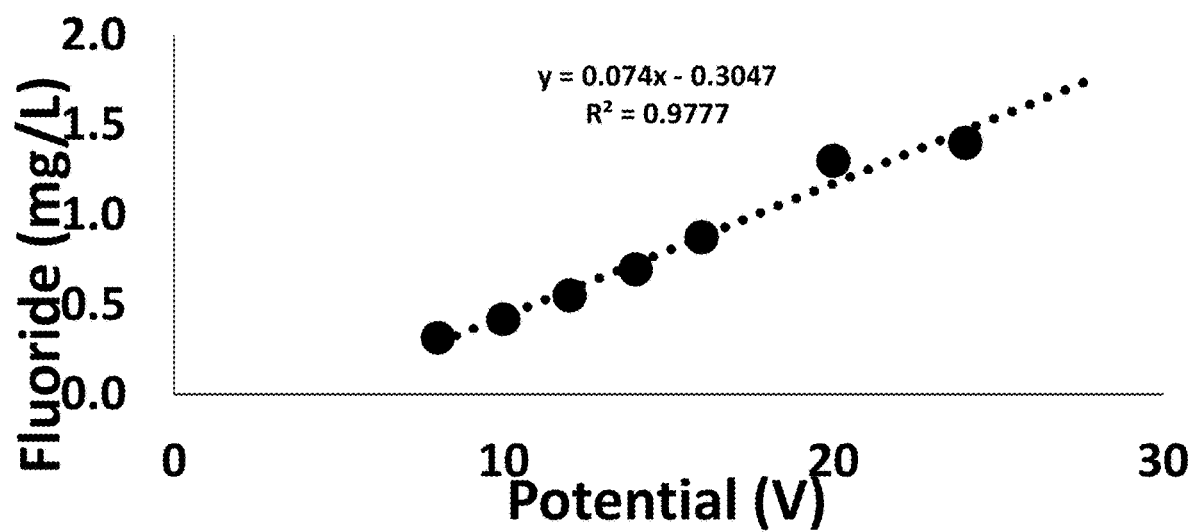
FIG. 4 illustrates example data of per fluoro octanoic acid (PFOA) oxidation on a BDD electrode.

Referring to FIG. 4, in an embodiment, example data of per fluoro octanoic acid (PFOA) oxidation on BDD electrode is illustrated. For example, PFOA, a PFAS compound, oxidation on a BDD electrode and fluoride measurement using a SPADNS test is shown. For example, a stopped flow oxidation may be performed with a duration of 300 seconds, a sample volume of about 5 mL, a conductivity of about 300 µS/cm, a PFOA concentration of about 40 ppm, EP grade BDD, and no Au/Ti back contacts. The digestion may be performed using voltage/current, mixing, and with mitigation of bubbles.

Figure 5:
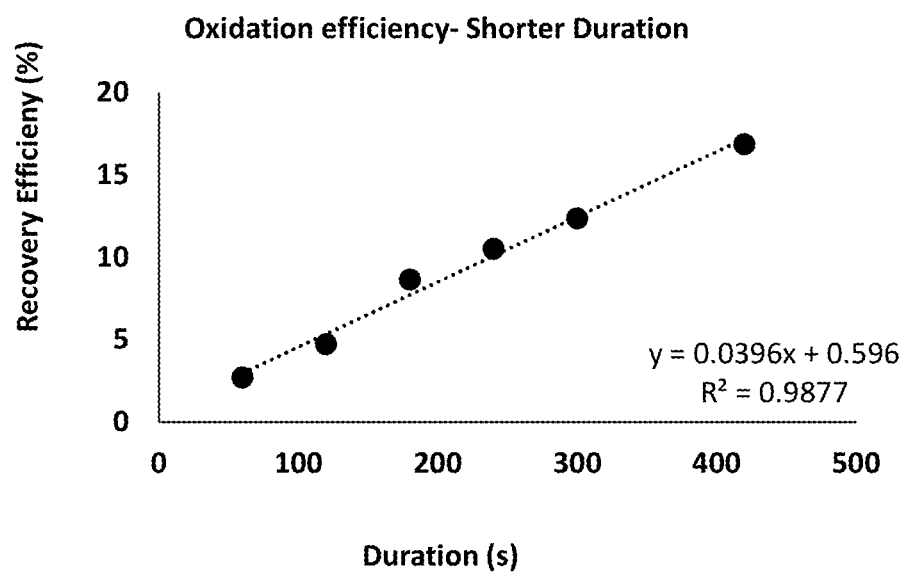
FIG. 5 illustrates example data of an oxidation efficiency for a shorter duration.
Figure 6:
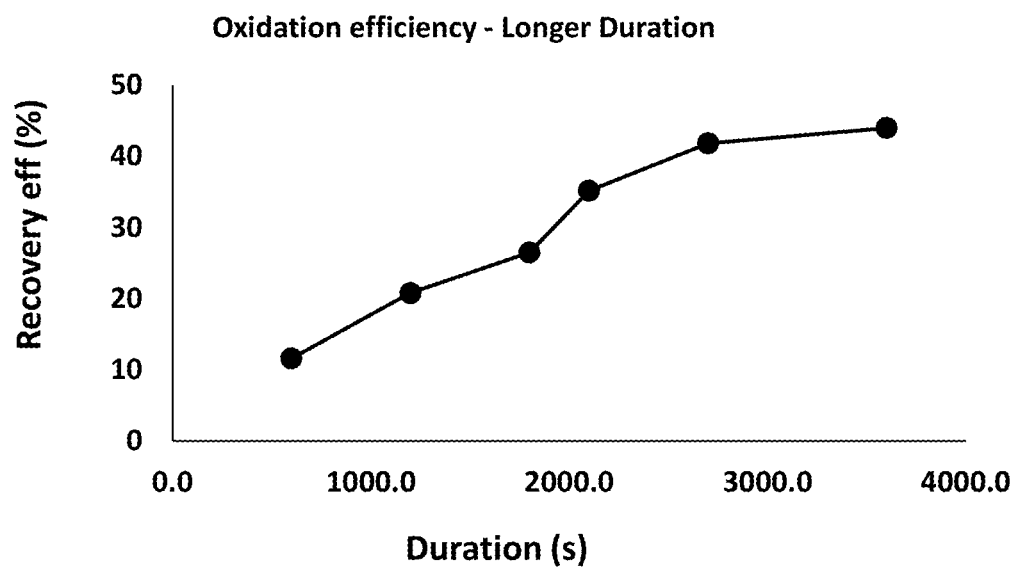
FIG. 6 illustrates example data of an oxidation efficiency for a longer duration.
Figure 7:
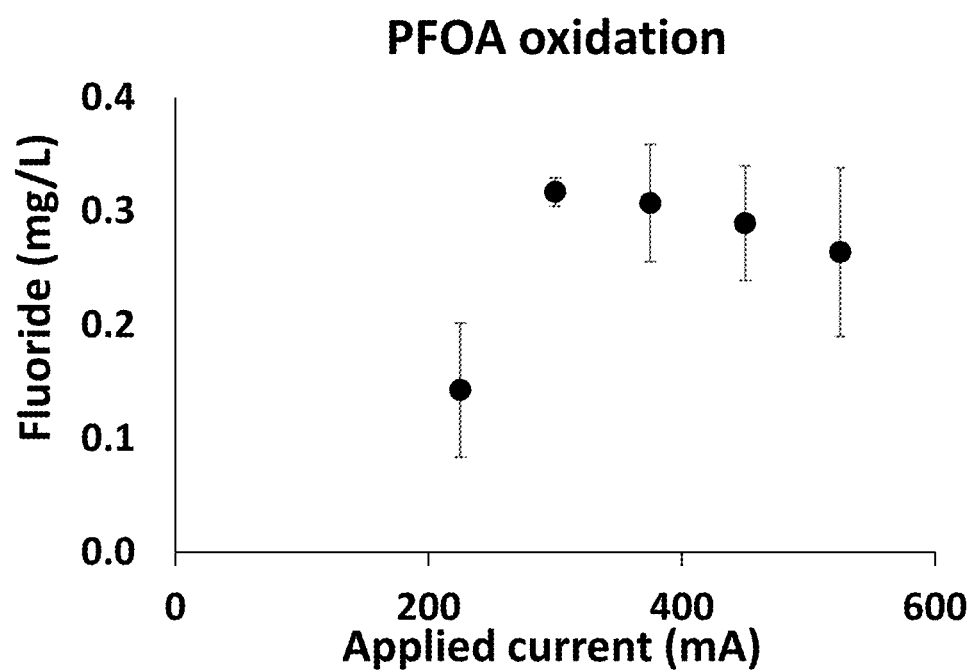
FIG. 7 illustrates an example PFOA oxidation plot.

Referring to FIG. 5, in an embodiment, an oxidation efficiency for a shorter duration is illustrated. A shorter duration may be less than 500 seconds. Referring to FIG. 6, in an embodiment, an oxidation efficiency for a longer duration is illustrated. A longer duration may be greater than 500 seconds. Both plots illustrate an increase in PFAS conversion efficiency to fluoride with increased oxidation time on a BDD electrode. Referring to FIG. 7, in an embodiment, an example PFOA oxidation plot is illustrated. For example, a concentration of fluoride (mg/L) is plotted over applied current in milliamps (mA). Examples are illustrative, as variables such as time, amperage, concentrations, flow rate, or the like may be adjusted based upon conditions.

Figure 8:
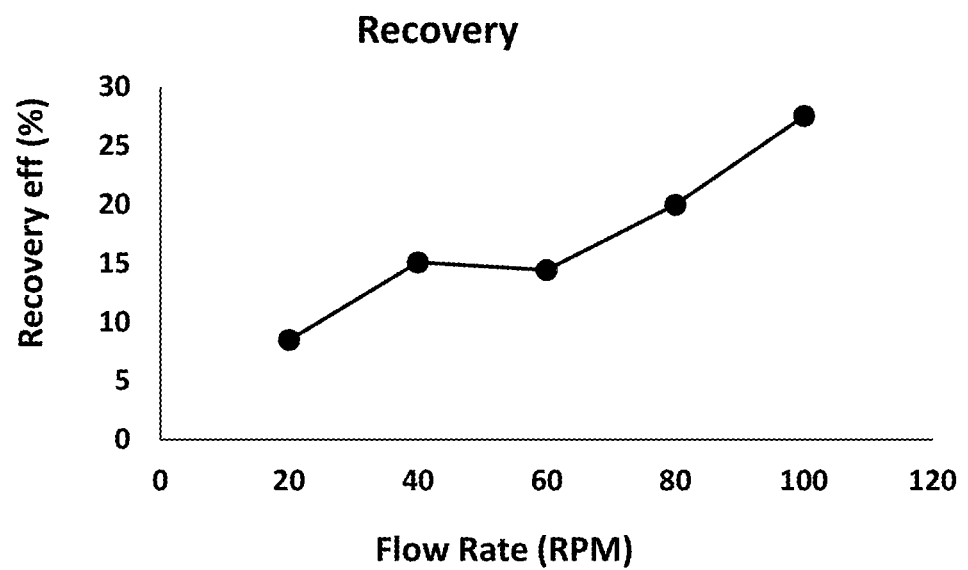
FIG. 8 illustrates an example relationship between flow rate and recovery efficiency.
Figure 9:
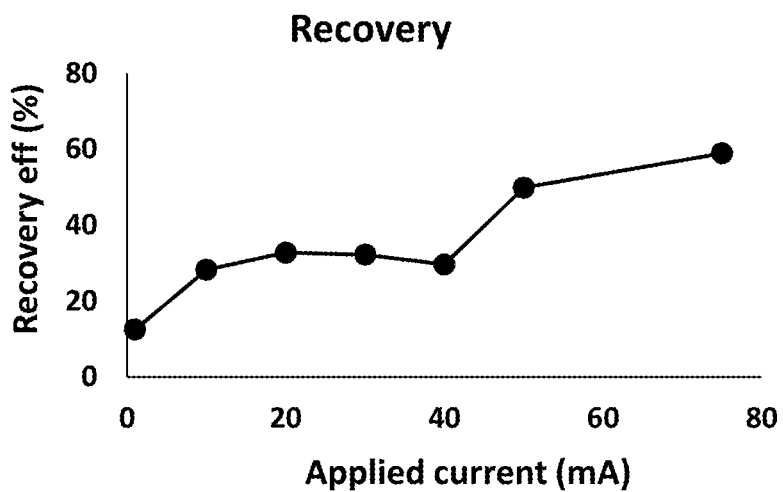
FIG. 9 illustrates an example relationship between applied current and recovery efficiency.

In an embodiment, other variables may be changed to allow for accurate measurement. For example, a flow rate of the method and system may be adjusted. Referring to FIG. 8, in an embodiment, an increase in flow rate (RPM) may increase recovery efficiency. As another example, applied current may be adjusted or increased. Referring to FIG. 9, in an embodiment, an increase in applied current (mA) may increase recovery efficiency. Examples are illustrative, as variables such as time, amperage, concentrations, flow rate, or the like may be adjusted based upon conditions.

Figure 10:
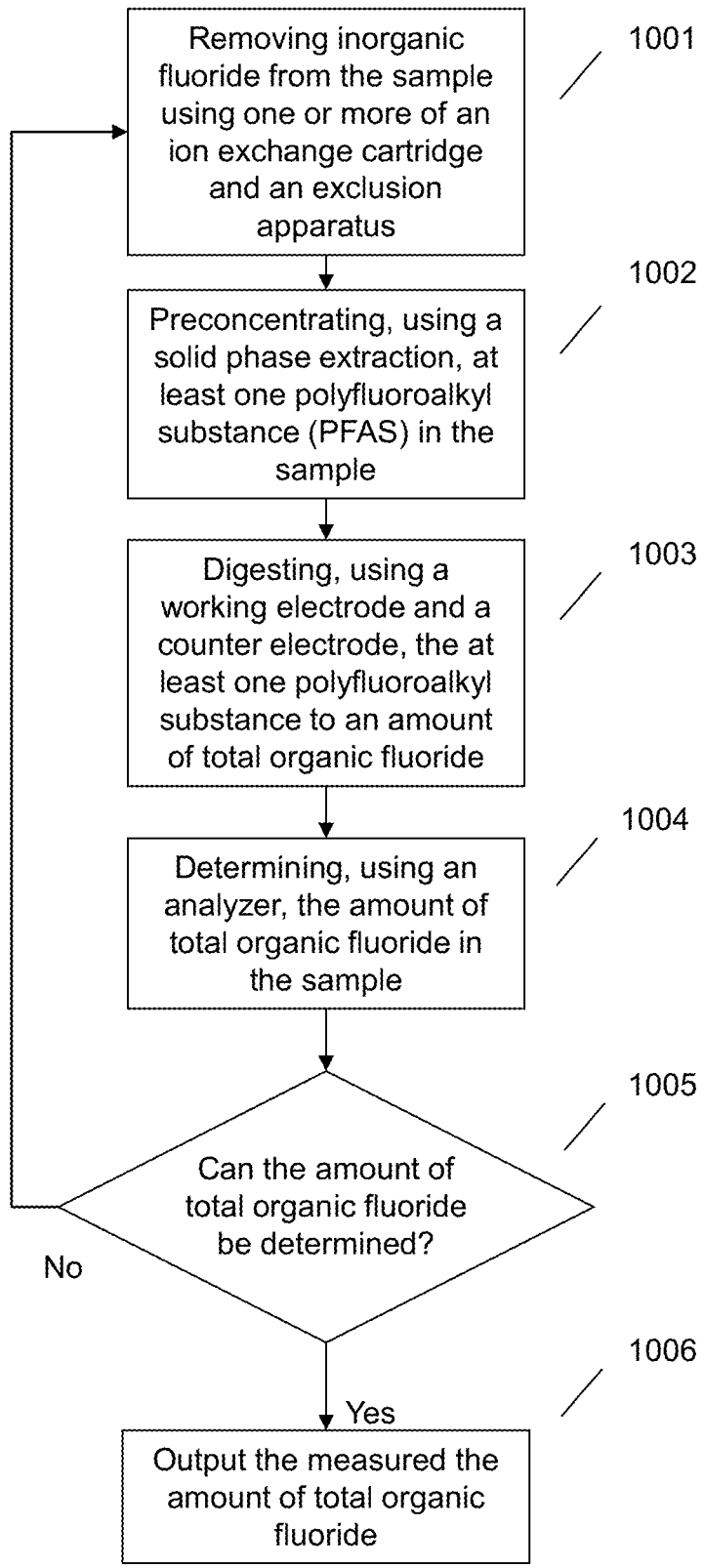
FIG. 10 illustrates a flow diagram of deriving PFAS substances from a total organic fluoride measurement.

Referring to FIG. 10, a flow diagram of an embodiment for measuring PFAS is illustrated. At 1001, inorganic fluoride may be removed from a sample. The removal may use an ion exchange resin or an exclusion method. At 1002, a sample with PFAS may be preconcentrated using solid phase extraction. At 1003, a PFAS substance may be digested in a digestion chamber. Further details of the digestion may be found thorough the specification. At 1004, in an embodiment, an analyzer may determine the total organic fluoride (TOF) in the sample. The TOF measurement may be correlated to an amount of PFAS present in the sample. An exclusion method to remove the inorganic fluoride consists of flowing the sample that contains both the PFAS and inorganic fluoride through as solid phase cartridge that is selective to PFAS. Inorganic fluoride anion is not retained in the cartridge. This the fluoride anion initially present in the sample is excluded from the cartridge. An eluent is used to extract the PFAS that is solely retained in the cartridge.

The method and system, at 1005, may determine an amount of TOF of the sample. If, however, the TOF may be determined at 1005, the system, at 1006, may output an amount of total organic fluoride, a PFAS concentration, or the like of the sample. The system may also output parameters such as flow rate, amperage, time of digestion, or the like. In an embodiment, an output may be in the form of a display, storing the data to a memory device, sending the output through a connected or wireless system, printing the output, or the like. The system may be automated, meaning the system may automatically output a measurement. The system may also have associated alarms, limits, or predetermined thresholds. For example, if a measured value reaches a threshold, the system may trigger an alarm, alert the system/personnel to a fault, alter the flow of the aqueous solution, or the like. Data may be analyzed in real-time, stored for later use, or any combination thereof. At 1006, if an amount of TOF cannot be determined, the system may obtain another sample for testing, output an alarm, send a reminder for maintenance, shunt the flow of sample, or the like.

The aqueous sample may be placed or introduced into a cartridge, digestion cell, or the like manually by a user or using a mechanical means, for example, gravity flow, a pump, pressure, fluid flow, or the like. For example, a water sample for testing may be introduced to a chamber by a pump. In an embodiment, there may be one or more chambers in which the one or more method steps may be performed. In an embodiment, valves or the like may control the influx and efflux of the sample into or out of the one or more chambers, if present. Once the sample is introduced to the measurement system, the system may measure a sample automatically.

In an embodiment, the electrodes may be fully or at least partially disposed in the volume of aqueous solution or sample. For example, if the sample is introduced into a chamber having one or more electrodes, the aqueous solution may at least partially cover the one or more electrodes. As another example, the one or more electrodes may be partially disposed within the chamber with the other portion of the electrode outside the chamber. Thus, when the aqueous solution is introduced into the chamber it only covers the portion of the electrodes that are within the chamber.

The various embodiments described herein thus represent a technical improvement to conventional methods and instrument for PFAS measurement. Using the techniques as described herein, an embodiment may use a method and device for an instrument for PFAS measurement. This is in contrast to conventional methods with limitations mentioned above. Such techniques provide a better method to construct and an instrument for PFAS measurement.

Figure 11:
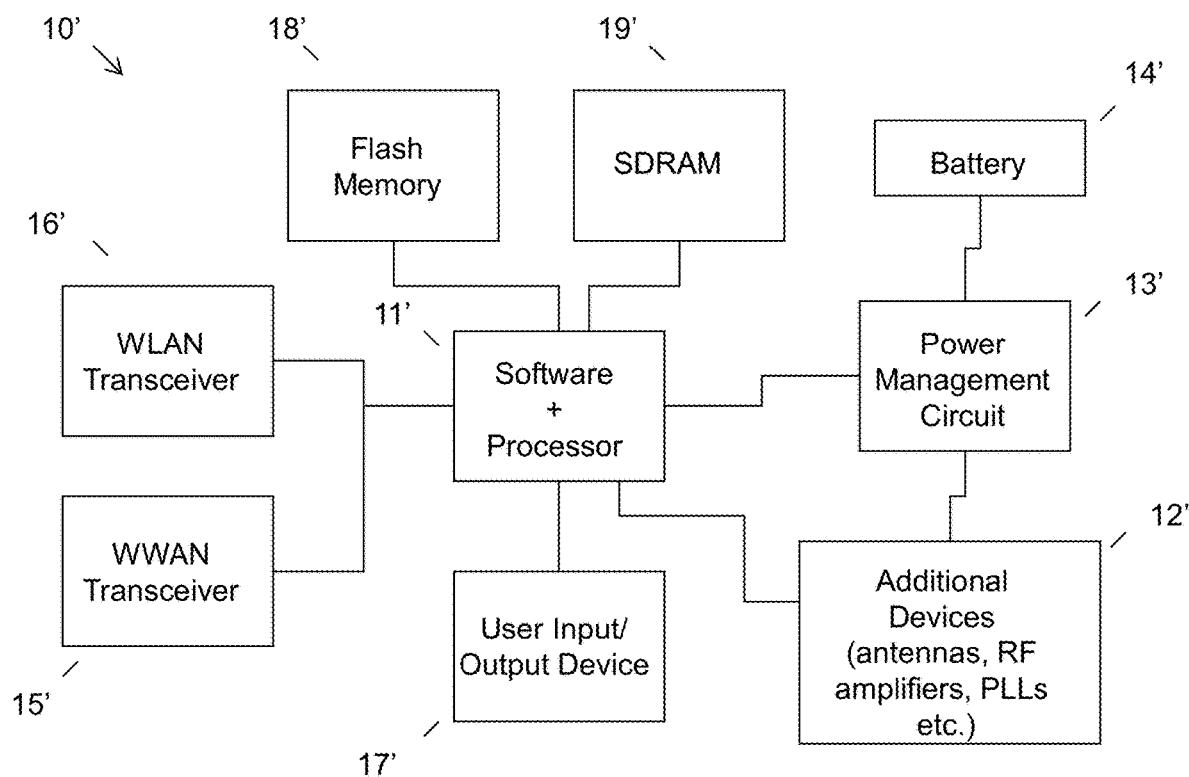
FIG. 11 illustrates an example of computer circuitry.

While various other circuits, circuitry or components may be utilized in information handling devices, with regard to an instrument for PFAS measurement according to any one of the various embodiments described herein, an example is illustrated in FIG. 11. Device circuitry 10' may include a measurement system on a chip design found, for example, a particular computing platform (e.g., mobile computing, desktop computing, etc.) Software and processor(s) are combined in a single chip 11'. Processors comprise internal arithmetic units, registers, cache memory, busses, I/O ports, etc., as is well known in the art. Internal busses and the like depend on different vendors, but essentially all the peripheral devices (12') may attach to a single chip 11'. The circuitry 10' combines the processor, memory control, and I/O controller hub all into a single chip 11'. Also, systems 10' of this type do not typically use SATA or PCI or LPC. Common interfaces, for example, include SDIO and I2C.

There are power management chip(s) 13', e.g., a battery management unit, BMU, which manage power as supplied, for example, via a rechargeable battery 14', which may be recharged by a connection to a power source (not shown). In at least one design, a single chip, such as 11', is used to supply BIOS like functionality and DRAM memory.

System 10' typically includes one or more of a WWAN transceiver 15' and a WLAN transceiver 16' for connecting to various networks, such as telecommunications networks and wireless Internet devices, e.g., access points. Additionally, devices 12' are commonly included, e.g., a transmit and receive antenna, oscillators, PLLs, etc. System 10' includes input/output devices 17' for data input and display/rendering (e.g., a computing location located away from the single beam system that is easily accessible by a user). System 10' also typically includes various memory devices, for example flash memory 18' and SDRAM 19'.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment of an instrument for PFAS measurement.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a measurement device such as illustrated in FIG. 11, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for deriving an amount of polyfluoroalkyl substances and perfluoroalkyl substances (PFAS) from a total organic fluoride measurement in a sample, comprising:
    preconcentrating, using a solid phase extraction, the amount of PFAS on a solid phase extraction device, wherein inorganic fluoride of the sample passes through the solid phase extraction device;
    digesting, using a working electrode and a counter electrode, the amount of PFAS to an amount of total organic fluoride; and
    determining, using an analyzer, the amount of total organic fluoride in the sample.

2. The method of claim 1, wherein the solid phase extraction is conducted on weak anion exchange materials to retain lower carbon chain PFAS from the sample.

3. The method of claim 1, wherein the solid phase extraction is conducted on a material selected from the group consisting of polymeric reverse phase and styrene divinylbenzene materials to retain higher carbon chain PFAS from the sample.

4. The method of claim 1, wherein the solid phase extraction excludes the inorganic fluoride from interfering in a PFAS analysis.

5. The method of claim 1, wherein at least one of the working electrode and the counter electrode is a free standing boron-doped diamond electrode.

6. The method of claim 1, wherein the working electrode oxidizes PFAS to protons, carbon dioxide, and fluoride.

7. The method of claim 1, wherein the working electrode indirectly oxidizes PFAS to carbon dioxide and fluoride using hydroxyl radicals, wherein the hydroxyl radicals are generated by water oxidation to produce hydrogen peroxide and oxygen.

8. The method of claim 1, wherein the working electrode indirectly oxidizes the amount of PFAS to carbon dioxide and fluoride using hydroxyl radicals, wherein the hydroxyl radicals are generated by hydrogen peroxide dissociation.

9. The method of claim 1, wherein the counter electrode reduces water to form hydroxide anions and hydrogen gas.

10. The method of claim 1, wherein the sample is recirculated across a digestion cell to ensure complete oxidation.

11. The method of claim 1, wherein the digesting is monitored during oxidation by measuring fluoride in a recirculation container.

12. The method in claim 1, wherein the digesting is enhanced by heating the sample reaching a recirculation container.

13. The method of claim 1, wherein the analyzer is selected from the group consisting of an optical measurement device, an electrochemical device, and a chromatographic device.

14. The method of claim 1, wherein the digesting uses a current density correlated to a length of carbon chains in the sample to differentiate PFAS of the amount of PFAS.

15. The method of claim 14, further comprising a separation of PFAS that separates PFAS having a carbon chain less than 5 carbons long from PFAS having a carbon chain greater than 5 carbons long.

16. The method of claim 1, wherein the amount of total organic fluoride correlates to an amount of PFAS in the sample.

17. The method of claim 1, wherein the digesting occurs in a recirculating cell.

18. A method for deriving an amount of polyfluoroalkyl substances and perfluoroalkyl substances (PFAS) from a total organic fluoride measurement in a sample, comprising:
    removing inorganic fluoride from the sample using an ion exchange cartridge;
    preconcentrating, using a solid phase extraction, the amount of PFAS on a solid phase extraction device;
    digesting, using a working electrode and a counter electrode, the amount of PFAS to an amount of total organic fluoride; and
    determining, using an analyzer, the amount of total organic fluoride in the sample.

* * * * *